US009947117B2

(12) United States Patent  (10) Patent No.: US 9,947,117 B2
Raupach  (45) Date of Patent: Apr. 17, 2018

(54) RECONSTRUCTION OF A RESULTANT IMAGE TAKING ACCOUNT OF CONTOUR SIGNIFICANCE DATA

(71) Applicant: Siemens Healthcare GmbH, Erlangen (DE)

(72) Inventor: Rainer Raupach, Heroldsbach (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 85 days.

(21) Appl. No.: 15/171,370

(22) Filed: Jun. 2, 2016

(65) Prior Publication Data

US 2016/0364889 A1  Dec. 15, 2016

(30) Foreign Application Priority Data

Jun. 15, 2015 (DE) ........................ 10 2015 210 912

(51) Int. Cl.
*G06K 9/00* (2006.01)
*G06T 11/00* (2006.01)
(Continued)

(52) U.S. Cl.
CPC .......... *G06T 11/003* (2013.01); *A61B 6/5205* (2013.01); *A61B 6/5211* (2013.01);
(Continued)

(58) Field of Classification Search
CPC ... A61B 6/5205; A61B 6/5258; A61B 6/5211; A61B 6/032; A61B 6/037; A61B 6/5217;
(Continued)

(56) References Cited

U.S. PATENT DOCUMENTS 5,640,436 A * 6/1997 Kawai .................. G06T 11/005
378/4
2005/0190984 A1   9/2005 Fischer
(Continued)

FOREIGN PATENT DOCUMENTS

DE  102004008979 A1  9/2005
DE  102005038940 A1  3/2007
DE  102011086456 A1  5/2013

OTHER PUBLICATIONS

Zhu L., etl.al.: "A Practical Reconstruction Atgorithm for CT Noise Variance Maps Using FBP Reconstruction", in SPIE, vol. 6510, 2007.
(Continued)

*Primary Examiner* — Gregory F Cunningham
(74) *Attorney, Agent, or Firm* — Harness, Dickey & Pierce, P.L.C.

(57) ABSTRACT

A method is disclosed for the reconstruction of resultant image data of an examination object from scan data acquired during a relative rotation movement between a radiation source of an X-ray image recording system and the examination object. An embodiment of the method includes reconstruction of initial image data from the scan data; derivation of contour data from the initial image data; calculation of contour significance data from the scan data and/or the initial image data; and calculation of the resultant image data using the contour data and the contour significance data. A corresponding computer program, a corresponding data carrier, a corresponding control and computation unit and a corresponding X-ray image recording system are also disclosed.

30 Claims, 4 Drawing Sheets

(51) Int. Cl.
*A61B 6/00* (2006.01)
*G06T 7/00* (2017.01)
*A61B 6/03* (2006.01)

(52) U.S. Cl.
CPC .......... *A61B 6/5217* (2013.01); *A61B 6/5258* (2013.01); *G06T 7/0012* (2013.01); *G06T 11/005* (2013.01); *A61B 6/032* (2013.01); *A61B 6/037* (2013.01); *G06T 11/008* (2013.01); *G06T 2207/10116* (2013.01)

(58) Field of Classification Search
CPC ................. G06T 11/003; G06T 7/0012; G06T 2207/10116; G06T 11/005; G06T 11/008
USPC ........................................................ 382/131
See application file for complete search history.

(56) References Cited

U.S. PATENT DOCUMENTS

2007/0040831 A1* 2/2007 Flohr ........................ G06T 5/50
345/424
2013/0121555 A1* 5/2013 Bruder .................. G06T 11/003
382/131

OTHER PUBLICATIONS

German Office Action dated Jan. 7, 2016.

* cited by examiner

FIG 5

RECONSTRUCTION OF A RESULTANT IMAGE TAKING ACCOUNT OF CONTOUR SIGNIFICANCE DATA

PRIORITY STATEMENT

The present application hereby claims priority under 35 U.S.C. § 119 to German patent application number DE 102015210912.7 filed Jun. 15, 2015, the entire contents of which are hereby incorporated herein by reference.

FIELD

At least one embodiment of the invention generally relates to a method for the reconstruction of resultant image data of an examination object from scan data, a corresponding computer program, a corresponding data carrier, a corresponding control and computation unit and/or a corresponding X-ray image recording system.

BACKGROUND

Medical imaging systems are distinguished in that internal structures of an examination object or patient can be investigated without having to carry out surgical interventions thereon.

Examples of such imaging systems or imaging equipment are ultrasonic systems, X-ray systems, X-ray computed tomography (CT) systems, positron emission tomography (PET) systems, single photon emission tomography (SPECT) systems or magnetic resonance (MR) systems.

In particular, X-ray image recording devices enable tomographic imaging wherein a number of projections of the object under investigation are recorded from different angles. From these projections, a two-dimensional sectional image or a three-dimensional volume image of the examination object can be computed.

An example of such a tomographic imaging system is the aforementioned X-ray CT. Methods for scanning an examination object with a CT system are commonly known. Herein, for example, circular scans, sequential circular scans with table advance or spiral scans are used. Other types of scanning, which do not involve circular movements are also possible, such as scans with linear segments. With the aid of at least one X-ray source and at least one detector arranged opposite thereto, X-ray attenuation data of the examination object are recorded from different recording angles and these attenuation data or projections thus gathered are used for computation via appropriate reconstruction methods to produce sectional images or three-dimensional images through the examination object.

Due to their non-invasive functioning, medical imaging devices nowadays play a significant part in the examination of patients. The representations of the internal organs and structures of a patient generated by the imaging systems are used for widely differing purposes, for example, preventative examinations (screening), for tissue sample taking (biopsy), for the diagnosis of the causes of illness, for planning and carrying out operations or for preparing therapeutic measures. In the field of radiation therapy, for example, radiological data are needed in order to plan the irradiation with regard to the distribution of the dose. Herein, the dose in the region to be treated must be above a threshold and in the remaining tissue, in particular in sensitive organs, it should be as low as possible in order to prevent secondary damage.

For this purpose and for many other of the abovementioned uses or tasks, the segmentation of particular target structures is useful and even required. Such target structures can be, for example, defined bone structures, particular organs, vessel structures or defects or lesions, for example, tumors which must first be identified and have possibly to be extracted from the image data.

Segmentation should be understood, in general, to mean the generation of regions of coherent content by grouping together adjacent image points according to a particular criterion. This criterion can be, for example, the belonging to a particular structure. The image data belonging to the structure can then, for example, be marked and/or virtually separated from the remaining image data and be considered separately or made available for further analyses.

A reliable and sufficiently accurate spatial separation of the segmentation of structures is essential for many uses.

Organs or lesions are identified by manual contouring or by automatic segmentation. Manual contouring, wherein an operator draws in border lines or border points while observing the image data on a screen with the aid of a graphical user interface, on the basis of which the segmentation then occurs, is more reliable with regard to the accuracy of the association of image points to structures and therefore applies, as before, as a reference. However, the time expenditure required for this is enormous since the markings have to be set by the user slice by slice.

Automatic segmentation algorithms enable, in principle, the time and personnel cost to be reduced and simultaneously the objectivity of the segmentation to be increased. Alongside primitive algorithms with linear edge detectors (Sobel-Scharr operator), enhanced algorithms take account of the statistical significance of contours, i.e. the segmentation weights the linear edge response with the background noise. However, the resolution and statistical properties in tomographic image data sets are non-trivial, i.e. the noise is non-stationary and anisotropic and the resolution is dependent on the position in the scanning field and the direction. Therefore, this consideration on the basis of the image data without additional information regarding the data acquisition succeeds only to a limited extent. Results of the automatic segmentation are therefore routinely corrected manually.

By contrast therewith, it is an object of the present invention to provide improved image data reconstructed from tomographic scan data which are suitable for a stable automatic segmentation via linear edge detection.

SUMMARY

At least one embodiment of the invention is directed to a method for the reconstruction of resultant image data, a corresponding computer program, a corresponding machine-readable data carrier, a control and computer unit for the reconstruction of resultant image data and a corresponding X-ray image recording system according to the alternative independent claims.

Embodiments of the invention described below are directed to a method and also a device. Features, advantages or alternative embodiments mentioned herein are also applicable similarly to the other claimed subject matter and vice versa. In other words, the present claims (which are directed, for example, to a device) can also be further developed with features disclosed or claimed with regard to a method. The corresponding functional features of the method are herein configured via suitable modules or units.

Embodiments of the invention include a concept that, with suitable manipulation of image data in the context of the image reconstruction, a subsequent automatic segmentation can be significantly simplified and thus configured to be more reliable. This succeeds in that statistical properties of the image data are not first taken into account in the context of the segmentation as additional information, but are included as early as during the reconstruction of the image data from the scan data or the raw data. In other words, the inventors have identified that the information content of reconstructed image data can be improved with regard to contours that are represented for a subsequent segmentation step in that contours contained in the image data are represented enhanced in a resultant image according to their statistical significance. The subsequent segmentation can thus dispense with additional information or knowledge about, for example, the data acquisition or image reconstruction.

Accordingly, at least one embodiment of the invention relates to a method for the reconstruction of resultant image data of an examination object from scan data which has been acquired during a relative rotation movement between a radiation source of an X-ray image recording system and the examination object, comprising:
reconstruction of initial image data from the scan data,
derivation of contour data from the initial image data,
calculation of contour significance data from the scan data and/or the initial image data,
calculation of the resultant image data using the contour data and the contour significance data.

According to a further embodiment, the method according to an embodiment of the invention is carried out iteratively. Herein, in each iteration step, the contour data weighted with the significance or a fraction thereof is added to the resultant image data of the preceding iteration step as a correction term according to the number of iterations. The iteration can be terminated, for example, after a previously specified number of iteration steps or alternatively when a previously specified termination criterion is fulfilled, for example, if the deviation between the resultant image data of the ultimate and penultimate iterations undershoot a previously defined value. In each iteration step, the initial image data can flow in, for example, in order to determine deviations of the current result thereof.

At least one embodiment of the invention also relates to a computer program with program code for carrying out all the method steps in accordance with the method according to an embodiment of the invention when the program is run in a computer. As a result, the method can be carried out on different computers reproducibly and less subject to error.

At least one embodiment of the invention relates also to a machine-readable data carrier on which the computer program described above is stored.

At least one embodiment of the invention further relates to a control and computation unit for the reconstruction of resultant image data of an examination object from scan data which has been acquired during a relative rotation movement between a radiation source of an X-ray image recording system and the examination object, comprising a program memory store for storing program code, wherein program code which carries out a method according to at least one embodiment of the invention is present in the program memory store.

At least one embodiment of the invention also relates to a control and computation unit for the reconstruction of resultant image data of an examination object from scan data which has been acquired during a relative rotation movement between a radiation source of an X-ray image recording system and the examination object, comprising
a reconstruction unit which is configured to reconstruct initial image data from the scan data,
a derivation unit which is configured to derive contour data from the initial image data,
a first computation unit which is configured to calculate contour significance data from the scan data and/or the initial image data, and
a second computation unit which is configured to calculate the resultant image data using the contour data and the contour significance data.

Finally, at least one embodiment of the invention relates to an X-ray image recording system with a control and computation unit according to at least one embodiment of the invention.

BRIEF DESCRIPTION OF THE DRAWINGS

The invention will now be described and explained in greater detail making reference to the example embodiments illustrated in the drawings. In the drawings.

DETAILED DESCRIPTION OF THE EXAMPLE EMBODIMENTS

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

Embodiments of the invention include a concept that, with suitable manipulation of image data in the context of the image reconstruction, a subsequent automatic segmentation can be significantly simplified and thus configured to be more reliable. This succeeds in that statistical properties of the image data are not first taken into account in the context of the segmentation as additional information, but are included as early as during the reconstruction of the image data from the scan data or the raw data. In other words, the inventors have identified that the information content of reconstructed image data can be improved with regard to contours that are represented for a subsequent segmentation step in that contours contained in the image data are represented enhanced in a resultant image according to their statistical significance. The subsequent segmentation can thus dispense with additional information or knowledge about, for example, the data acquisition or image reconstruction.

Accordingly, at least one embodiment of the invention relates to a method for the reconstruction of resultant image data of an examination object from scan data which has been acquired during a relative rotation movement between a radiation source of an X-ray image recording system and the examination object, comprising:
reconstruction of initial image data from the scan data,
derivation of contour data from the initial image data,
calculation of contour significance data from the scan data and/or the initial image data,
calculation of the resultant image data using the contour data and the contour significance data.

The scan data corresponds to the raw data or X-ray projections acquired via an X-ray detector. From it, initial image data is generated via a "neutral" reconstruction. The initial image data can be a two-dimensional or three-dimensional image data set. The "neutral" reconstruction corresponds to a conventional known reconstruction method which is usable in a reconstruction for diagnostic purposes. The reconstruction method can be selected so that the initial image data is neutral with regard to the contour information included. This means that the contours included cannot be, for example, enhanced or, more generally expressed, manipulated by the reconstruction. From the initial image data, contour data can subsequently be derived. This represents all the edges and contours derived in the initial image data according to their position and direction. Derivation should be understood to mean any analysis, manipulation or evaluation of the initial image data that is suitable for determining the contour data. In a further step of the method, contour significance data is calculated. The inventor has discovered that this can be determined, first, from the initial image data and, secondly, directly from the scan data. Both the contour data and also the contour significance data is subsequently used in the calculation of the resultant image data.

Insofar as it is not pre-defined by the method according to at least one embodiment of the invention, the sequence of the steps included is arbitrary and variable.

The calculation of the contour significance data as a step of an image reconstruction provides full knowledge regarding the resolution and the statistical properties of the image data. In particular, in this way, anisotropic or directional noise effects can be taken into account already in the context of the reconstruction, which significantly increases the reliability of the significance of detected structures.

According to one embodiment of the invention, the calculation of the contour significance data comprises calculation of local contour information from the initial image data. The expression "local" signifies that the contour information is considered individually for individual image regions or image parts. An image region can be, for example, an image element, i.e. a pixel or a voxel, but also an area in the image which is formed by a plurality of, for example, adjacent or at least coherent image elements.

According to a further embodiment, the local contour information comprises the contour amplitude and/or the contour direction.

This contour information can be obtained, for example, in that a simple edge detector is applied to the initial image data. The detection filter observes and identifies intensity changes in the initial image data and creates therefrom the contour information such that image elements or image regions with a stronger intensity change are recognized in the initial image data as a contour and, for example, newly assigned a high intensity value corresponding to the intensity change. For example, the edge detector corresponds to a folding of the initial image data with a filter matrix. For example, the edge detector can be an operator from the class of "identity minus low-pass filters", in particular a Scharr or Sobel operator. The contour amplitude herein does not correspond directly to the filtration, but represents a scalar measure of the amount of the direction-dependent contributions. The contour direction results, for example, from the direction components of the edge detector, each of which describes the change in a particular spatial direction, for example $K_x(x,y,z)$, $K_y(x,y,z)$, $K_z(x,y,z)$ as the change along the Cartesian axes, or written more compactly as a vector, $\vec{K}(x,y,z)=(K_x(x,y,z),K_y(x,y,z),K_z(x,y,z))$. The contour amplitude is given as the magnitude of the vector, that is $|\vec{K}|= \sqrt{K_x^2+K_y^2+K_z^2}$, wherein the spatial dependency has been omitted for reasons of clarity.

According to a further embodiment of the invention, the calculation of the contour significance data comprises a calculation of local statistical information in the initial image data. The expression "local" also signifies, in relation to the statistical information, individual image regions or image parts or, more generally, the position in space. Herein also, an image region can be, for example, an image element, i.e. a pixel or a voxel, but also an area in the image which is formed by a plurality of, for example, adjacent or at least coherent image elements. In addition, the expression "local" also signifies in this context the direction-dependence of the statistical information. In this way, the anisotropy of the noise in the initial image data can be taken into account. Through the determination of statistical information, statistical properties are already taken into account in the context of the reconstruction.

According to a further embodiment, the local statistical information is the local standard deviation of the noise. For determination thereof, firstly, image-based approaches are available, such as described in the patent applications DE 10 2004 008 979 or DE 10 2005 038 940, the entire contents of the disclosure of which is hereby incorporated herein by reference and is expressly included fully within the present application. Alternatively, the variance of the scan data can be analyzed and therefrom the local standard deviation can be derived. For this purpose, the method described, for example, in Proc. SPIE 6510, Medical Imaging 2007: Physics of Medical Imaging, 651023 (Mar. 14, 2007; doi: 10.1117/12.713692), the entire contents of the disclosure of which is also hereby incorporated herein by reference and is expressly included fully within the present application, is available. In particular, the evaluation of the scan data to determine the local standard deviation of the noise enables the directional dependency of the noise to be taken into account. Alternatively to the local standard deviation, in the context of the invention, the variance of the noise or variables derivable therefrom, for example, percentiles can also be taken into account as statistical information.

According to a further embodiment, the calculation of the contour significance data comprises the determination of a contour-to-noise ratio. This is found, for example, as the quotient of the local contour information and the local statistical information. The contour-to-noise ratio corresponds to a signal-to-noise ratio and places the local contour information in relation to the local statistical information. In other words, the contour-to-noise ratio normalizes the edge signal in the image data to the noise.

According to a further embodiment of the invention, the calculation of the contour significance data comprises formation of the contour-to-noise ratio via a restricted significance function to a value between 0 and 1. By way of this step, the method according to an embodiment of the invention discriminates between contours in the image data which are significant or insignificant in relation to the noise, in that it images the contour-to-noise ratio to a significance of between 0 and 1. Significant contours are visible in the background noise, whereas insignificant contours do not stand out from the noise signal. The significance function $f(t)$ is restricted in the sense that $$f(0)=0 \text{ and } \lim_{t\to\infty} f(t)=1.$$

According to a further embodiment, the significance function $f(t)$ is configured as a continuous function or a step function. The significance function $f(t)$ in the form of a step function decides strictly, by way of its threshold, regarding the relevance of a contour.

According to a further embodiment of the invention, the significance function $f(t)$ takes the following form:

$$f(t)=1-\exp(-(t/c)^2),$$

wherein the parameter c determines the transition between significant and insignificant. In addition, any number of other functions are conceivable.

According to a further embodiment, the derivation of the contour data comprises a high-pass filtration of the initial image data. The high-pass filtered image data represents a differential signal corresponding to the direction or orientation of an edge or contour. Thus, everywhere that an edge is situated in the initial image data, the high-pass filtration ensures an emphasizing of this edge in the contour data. A characteristic of the contour data is the "light-dark border" along the extent of a contour.

According to a further embodiment of the invention, the high-pass filtration has a frequency response the transmission of which disappears at the spatial frequency 0 and increases with increasing spatial frequency greater than 1. In other words, low spatial frequencies are eliminated or suppressed by the high-pass filter, whereas higher spatial frequencies, that is edge and contour information in the initial image data, are amplified. The high-pass filtration therefore provides for emphasizing contours in the contour data.

According to a further embodiment of the invention, the resultant image data are formed on the basis of the product of the contour data and the contour significance data. This procedure corresponds to the calculation of a contour image weighted with the contour significance data. The multiplication takes place, for example, for each image element or each image region.

According to an alternative embodiment of the invention, the resultant image data is formed on the basis of the sum of the initial image data and the product of the contour data and the contour significance data. According to this embodiment, the resultant image data corresponds to a contour image which has contours emphasized depending on the local significance. In contrast to the contour image in this case, the previous contour image weighted according to the significance is usable only conditionally for diagnostic purposes due to its significant deviation of the image properties relative to the initial image data. With regard to the subsequent segmentation algorithm, however, the resultant image data of both alternatives provides comparable improvements, since both supply the same information on analysis of differential signals, for example via simple edge detectors. The segmentation in the context of the post-processing can now be simplified. This succeeds since information regarding the significance of structures is already contained in the resultant image data in the form of a selective edge enhancement. Edge detection can now be carried out easily via a linear edge detector and an associated threshold using the resultant image data.

According to a further embodiment, the method according to an embodiment of the invention is carried out iteratively.

Herein, in each iteration step, the contour data weighted with the significance or a fraction thereof is added to the resultant image data of the preceding iteration step as a correction term according to the number of iterations. The iteration can be terminated, for example, after a previously specified number of iteration steps or alternatively when a previously specified termination criterion is fulfilled, for example, if the deviation between the resultant image data of the ultimate and penultimate iterations undershoot a previously defined value. In each iteration step, the initial image data can flow in, for example, in order to determine deviations of the current result thereof.

At least one embodiment of the invention also relates to a computer program with program code for carrying out all the method steps in accordance with the method according to an embodiment of the invention when the program is run in a computer. As a result, the method can be carried out on different computers reproducibly and less subject to error.

At least one embodiment of the invention relates also to a machine-readable data carrier on which the computer program described above is stored.

At least one embodiment of the invention further relates to a control and computation unit for the reconstruction of resultant image data of an examination object from scan data which has been acquired during a relative rotation movement between a radiation source of an X-ray image recording system and the examination object, comprising a program memory store for storing program code, wherein program code which carries out a method according to at least one embodiment of the invention is present in the program memory store.

At least one embodiment of the invention also relates to a control and computation unit for the reconstruction of resultant image data of an examination object from scan data which has been acquired during a relative rotation movement between a radiation source of an X-ray image recording system and the examination object, comprising
  a reconstruction unit which is configured to reconstruct initial image data from the scan data,
  a derivation unit which is configured to derive contour data from the initial image data,
  a first computation unit which is configured to calculate contour significance data from the scan data and/or the initial image data, and
  a second computation unit which is configured to calculate the resultant image data using the contour data and the contour significance data.

Finally, at least one embodiment of the invention relates to an X-ray image recording system with a control and computation unit according to at least one embodiment of the invention.

Figure 1:
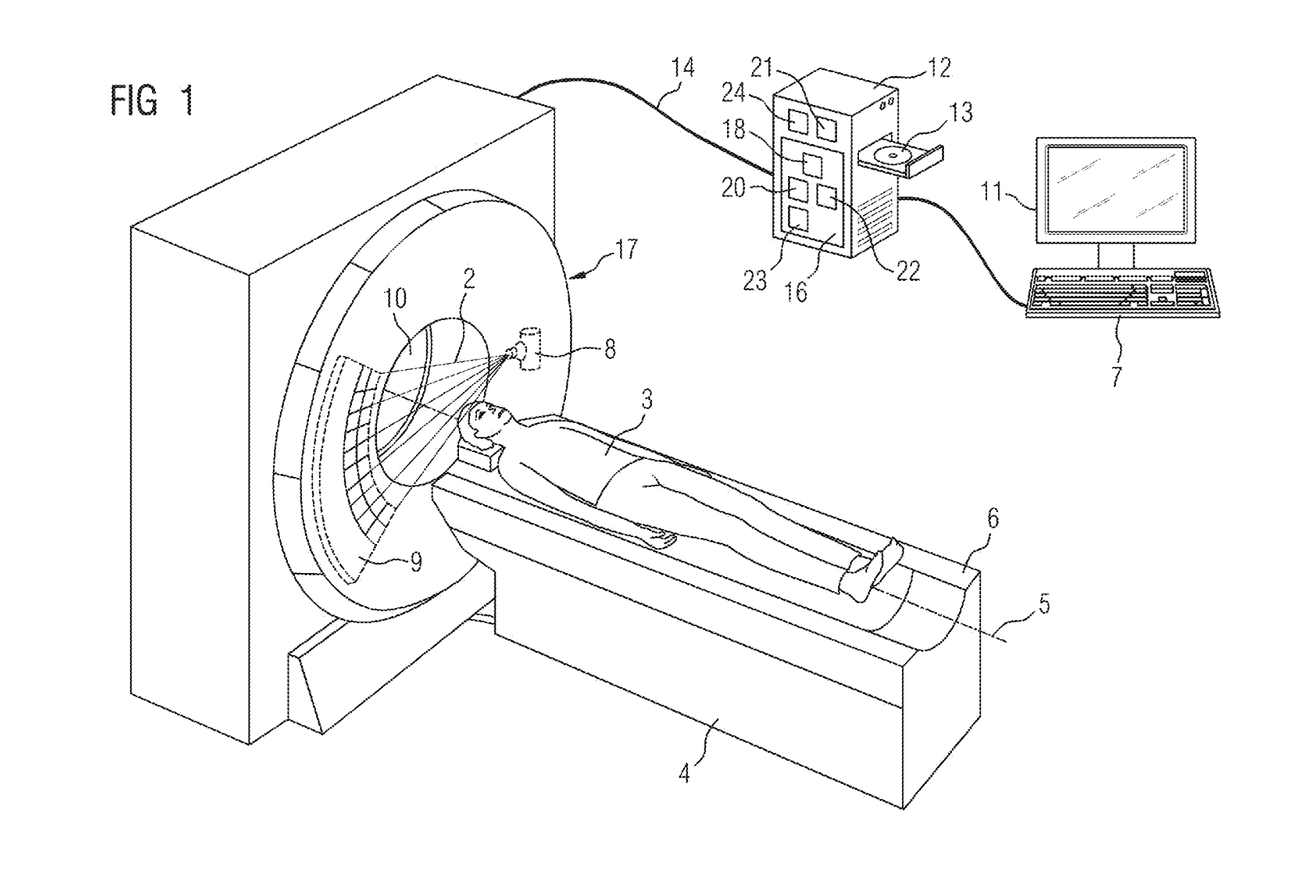
FIG. 1 is an X-ray image recording device according to an example embodiment of the invention.

FIG. 1 shows an X-ray image recording device using the example of an X-ray computed tomography device. The computed tomography device shown here has a recording unit 17 comprising a radiation source 8 in the form of an X-ray source and a radiation detector 9 in the form of an X-ray detector. The recording unit 17 rotates during the recording of X-ray projections about a system axis 5 and, during the recording, the X-ray radiation source emits rays 2 in the form of X-rays. The X-ray radiation source is an X-ray tube. The X-ray radiation detector is a linear detector with a plurality of rows.

During the recording of projections, the examination object 3, here a patient, lies on a patient support 6. The patient support 6 is connected to a support base 4 such that the support base 4 carries the patient support 6 with the patient 3. The patient support 6 is configured to move the patient 3 along a recording direction through the opening 10 of the recording unit 17. The recording direction is typically given by the system axis 5 about which the recording unit 17 rotates during the recording of X-ray projections. During a spiral scan recording, the patient support 6 is moved continuously through the opening 10 while the recording unit 17 rotates round the patient 3 and records projection data. Thus the X-rays describe a helix on the surface of the patient 3.

The X-ray image recording device has a computer system 12 in the form of a computer which is connected to a display unit 11, for example, for graphical display of reconstructed X-ray image recordings, for example, a reconstructed image data set, and an input unit 7. The display unit 11 can be, for example, an LCD, plasma or OLED screen. It can also be a touch-sensitive screen which is further configured as an input unit 7. A touch-sensitive screen of this type can be integrated into the imaging device or configured as part of a mobile device. The input unit 7 is, for example, a keyboard, a mouse, a touch screen or a microphone for speech input. The input unit 7 can also be configured to recognize movements of a user and to convert them into corresponding commands.

The computer system 12 is connected to the rotatable recording unit 17 for data exchange. Via an interface unit 21 and the connection 14, firstly, control signals for the X-ray image recording are transferred from the computer system 12 to the recording unit 17. For this purpose, different scan protocols, each matched to an examination type can be stored in a memory store 24 and selected by the user before the projection data recording. The control of the recording unit 17 takes place according to the selected scan protocol. Alternatively, recorded scan data MD in the form of projection data for further processing is acquired via the interface unit 21 in a control and computation unit 16 which is described in greater detail below or the corresponding individual components. The connection 14 is realized in the known manner cable-bound or cable-free.

The computer system 12 comprises a reconstruction unit 23 which is configured to reconstruct initial image data IBD in the form of an image data set from the scan data MD according to known reconstruction methods. One or more reconstruction algorithms can be stored for this purpose in a memory store 24 of the computer system 12 for the reconstruction unit 23 to call up or for selection by the reconstruction unit 23.

The computer system 12 comprises a derivation unit 22 which processes the initial image data IBD so that it generates contour data KD therefrom. For this purpose, the derivation unit 22 uses, for example, a suitable high-pass filter H on the initial image data IBD, as described in greater detail below. In order to provide the initial image data IBD, the derivation unit 22 is in data connection to the reconstruction unit 23.

The computer system 12 also comprises a first computation unit 20 which is configured to calculate contour significance data KSD from the initial image data IBD and/or from the scan data MD. For this purpose, the first computation unit 20 is in data connection to the interface unit 21 to receive the scan data MD and to the reconstruction unit 23 to receive the initial image data IBD. The first computation unit 20 is configured, firstly to determine local contour information LKI, for example, in the form of the contour amplitude and/or contour direction and, secondly to determine local statistical information LSI, for example, in the form of the local standard deviation of the noise. For this purpose, the first computation unit 20 uses necessary data or image processing steps either on the initial scan data ID or the measurement data MD, as described in greater detail below. Furthermore, the first computation unit 20 is also configured to calculate a contour-to-noise ratio KNSR from the calculated local contour information LKI and the calculated local statistical information LSI and to image this by way of a significance function f(t) to a significance value between 0 and 1. For this purpose, the first computation unit 20 is connected to the storage memory 24 in which the different possible significance functions f(t) are stored for call up by the first computation unit 20. Depending on the use, the possibility therefore exists for adapting the significance function f(t).

In addition, the computer system 12 also comprises a second computation unit 18 which is configured to calculate resultant image data EBD from the contour data KD and the contour significance data KSD. This data is distinguished by contours shown emphasized according to the local contour significance. The second and the first computation unit 18 and 20 are also in data connection.

In the present case, the reconstruction unit 23, the derivation unit 22, the first and the second computation unit 20 and 18 are configured as separate modules within the computer system 12 which, where required, are in data-exchanging communication with one another. Alternatively, all the named units can, for example, also be integrated into the control and computation unit 16, whether in the form of a physical or a functional integrity.

The computer system 12 can cooperate with a computer-readable data carrier 13, in particular, in order to carry out a method according to an embodiment of the invention via a computer program with program code. Furthermore, the computer program can be stored on the machine-readable carrier, so as to be callable. In particular, the machine-readable carrier can be a CD, DVD, Blu-Ray disc, memory stick or a hard disc drive. The reconstruction unit 23, the derivation unit 22, the first and second computation unit 20 and 18 or the control and computation unit 16 can be configured in the form of hardware or software. For example, the control and computation unit 16 is configured as an FPGA (Field Programmable Gate Array) or comprises an arithmetic logic unit.

In the example shown here, at least one computer program is stored in the memory store 24 of the computer system 12 which carries out all the method steps of the method according to an embodiment of the invention when the program is carried out on the computer. The computer program for carrying out the method steps of the method according to an embodiment of the invention comprises program code. Furthermore, the computer program can be configured as an executable file and/or can be stored on a computer system other than the computer system 12. For example, the X-ray imaging device can be configured such that the computer system 12 loads the computer program into its internal working memory to carry out the method according to an embodiment of the invention via an intranet or via the Internet.

Figure 2:
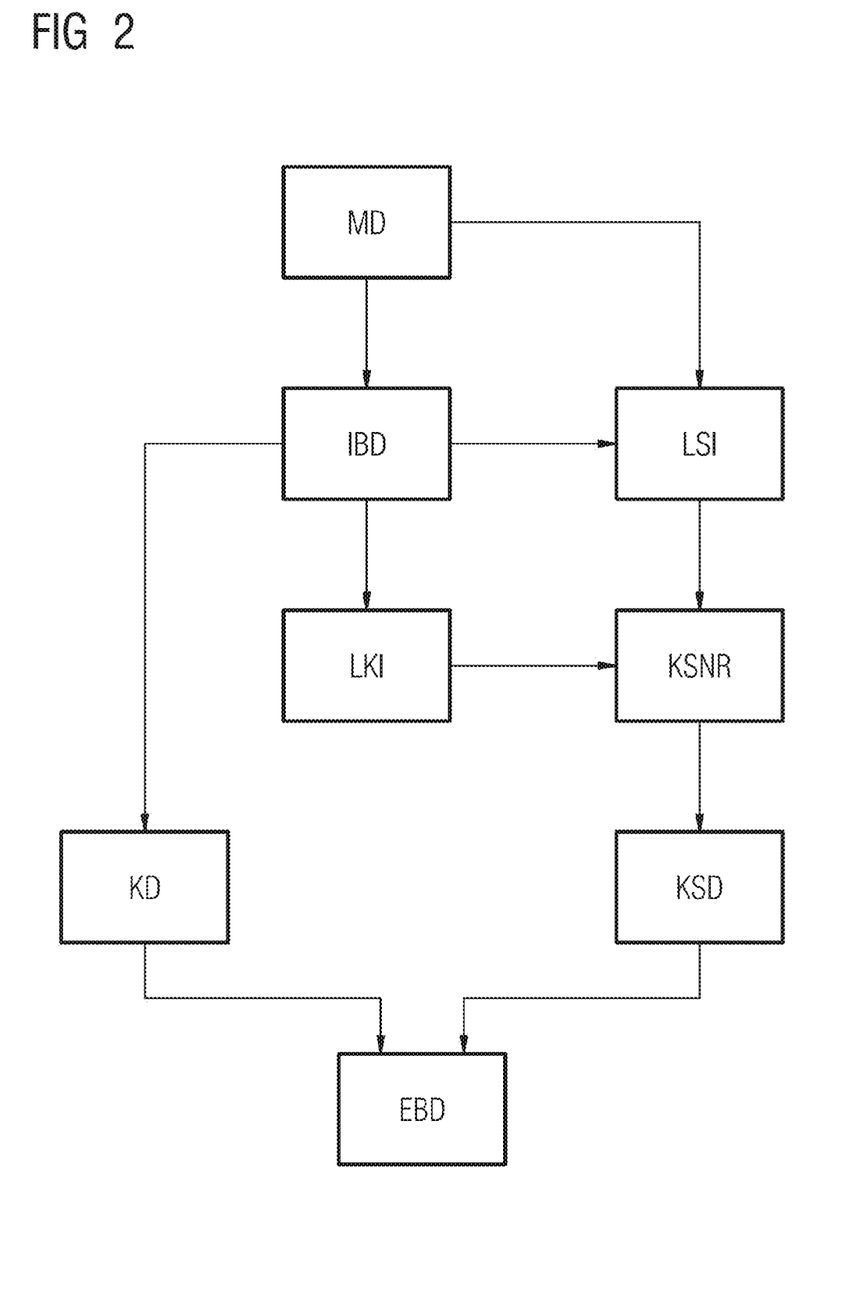
FIG. 2 is the method according to an embodiment of the invention as a block diagram according to an example embodiment of the invention.

FIG. 2 shows the method according to an embodiment of the invention in a possible example embodiment as a block diagram. Scan data MD are present in the form of a plurality of projections acquired from different directions. These are converted via a known reconstruction method which does not itself bring about any edge enhancement, for example, a filtered back projection (FBP), into initial image data IBD in the form of an image data set. Contained in the scan data MD and the initial image data IBD is information relating to the resolution and statistics of the data set which is not taken into account in the context of a conventional reconstruction and then is no longer available for the image post-processing. The method according to an embodiment of the invention takes account of this information.

In particular, the method according to an embodiment of the invention takes account of direction-dependent effects, i.e. directional noise. This information is extracted with the following steps of the method and made usable for post-processing steps. A linear edge detector is used on the initial image data set IBD, in order to obtain local contour information LKI. From the initial image data set IBD or from the scan data MD, in addition local statistical information LSI is obtained.

In this example embodiment, this involves the local standard deviation of the noise in the data set. The local contour information LKI is then normed to the local statistical information LSI, so that a contour-to-noise ratio KNSR results which is used for determining the local contour significance data KSD. The contour significance data KSD is a measure for whether a contour or edge in the initial image data IBD stands out significantly from the noise in the image data or disappears therein. The initial image data IBD is also used to determine contour data KD in the form of a contour data set. This takes place through the use of a high-pass filter H on the initial image data IBD. The high-pass filtration generates a differential edge signal. Contrasted therewith, the local contour information LKI represents a scalar variable. The contour data KD is finally weighted with the contour-significance data KSD.

By this, resultant image data EBD are generated which represent significance-dependently enhanced contour progressions. The resultant image data EBD are therefore suitable to a particular degree for feeding to a simple linear edge detection.

Figure 3:
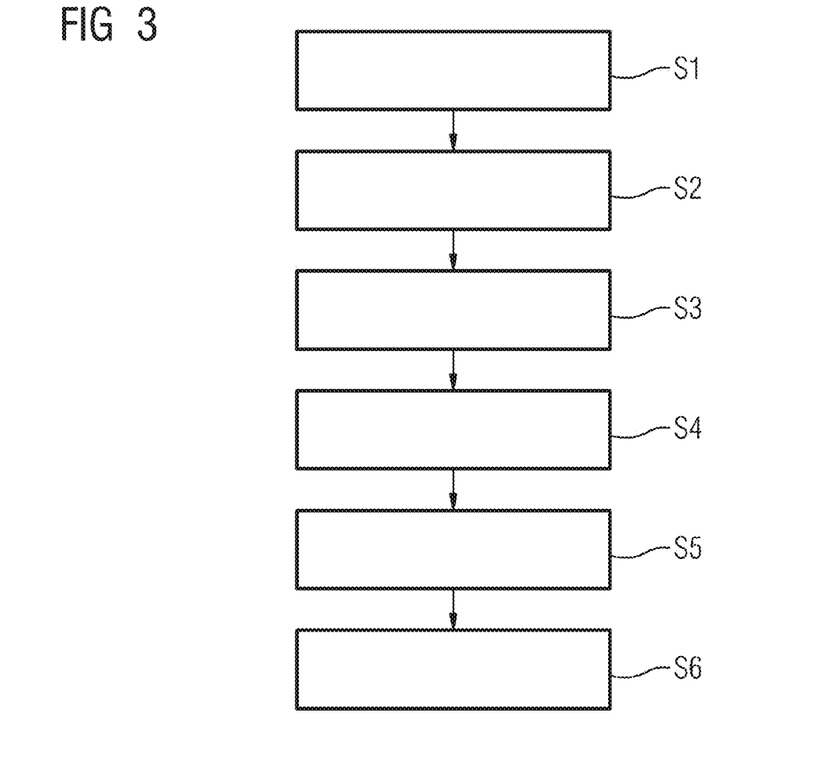
FIG. 3 is a schematic sequence of the method according to an embodiment of the invention according to an example embodiment of the invention.

FIG. 3 shows the method according to an embodiment of the invention in an example embodiment as a flow diagram. The first step S1 reconstructs from a plurality of projections of an image data recording, a neutral three-dimensional image data set I(x,y,z), wherein x,y,z denote the coordinates of each voxel in the image data. The image data set is neutral in the sense that, through the reconstruction, it has itself experienced no edge enhancement.

As previously mentioned, a filtered back projection can be used and other reconstruction algorithms are also possible. Via a simple linear edge detector, for example, a Sobel operator, in step S2, the local edge amplitude K(x,y,z) and additionally the local direction of the edge $\vec{e}_K(x,y,z)$ are calculated. The direction of the edge is given, for example, by the directional selectivity of the filter used. Thus, for the Sobel operator a filter mask would be used for horizontal, vertical and/or diagonal edges.

The direction of the edge $\vec{e}_K(x,y,z)$ is defined, for example, for each voxel entirely by the normal vector $\vec{e}_K = \vec{K}/|\vec{K}|$. The edge detector acts like a filter which is applied in the configuration space with a convolution operation on a voxel and its adjacent voxels. The size of the environment of the voxel included in the filtration is determined by the filter itself and can change accordingly. As an alternative to the configuration space, the edge detection can be carried out via Fourier transform of the entire image volume, multiplication by the frequency representation of the filter and inverse Fourier transform also in the frequency space. The procedure is directed in general to the size of the image volume and of the design of the filter.

In step S3 of the method, the local standard deviation of the noise $\sigma(\vec{e};x,y,z)$ to be expected is determined. For this purpose, either the image data I(x,y,z) can be accessed wherein, for example, as in DE 10 2004 008 979 A1 (the entire contents of which are hereby incorporated herein by reference), one-dimensional variances are determined for each voxel in a particular spatial region or radius R starting from the observed voxel, for numerous spatial directions, preferably isotropically distributed in space, from which the respective standard deviation can be derived in known manner by root formation.

Alternatively, the determination of the local, direction-dependent standard deviation $\sigma(\vec{e};x,y,z)$ is carried out on the basis of the projections. Alternatively, $\sigma(\vec{e};x,y,z)$ is determined only for rough directions $\vec{e}$, wherein (x,y,z) describe a relatively coarser grid than that of the image data. The determination of $\sigma(\vec{e}_K(x,y,z);x,y,z)$, as is necessary for calculating the significance, would then take place via interpolation, for example, multi-linearly of the pre-calculated coarse sampling points. This procedure proves to be significantly faster and memory space-saving. In a further step S4, the local contour significance S(x,y,z) is calculated from the local contour amplitude K(x,y,z) and the direction-dependent local standard deviation $\sigma(\vec{e}_K(x,y,z);x,y,z)$ with $$x,y,z = f(K(x,y,z)\sigma \vec{e}_K(x,y,z);x,y,z;x,y,z)$$

wherein the significance function $f(t)$ takes the form $f(t) = 1 - \exp(-(t/c)^2)$. Alternative significance functions with a value range of between 0 and 1 are also possible. The contour significance S(x,y,z) takes account of the quotients from local contour amplitudes K(x,y,z) and the direction-dependent local standard deviation $\sigma(\vec{e}_K(x,y,z);x,y,z)$. This corresponds to a normalization step.

Figure 4:
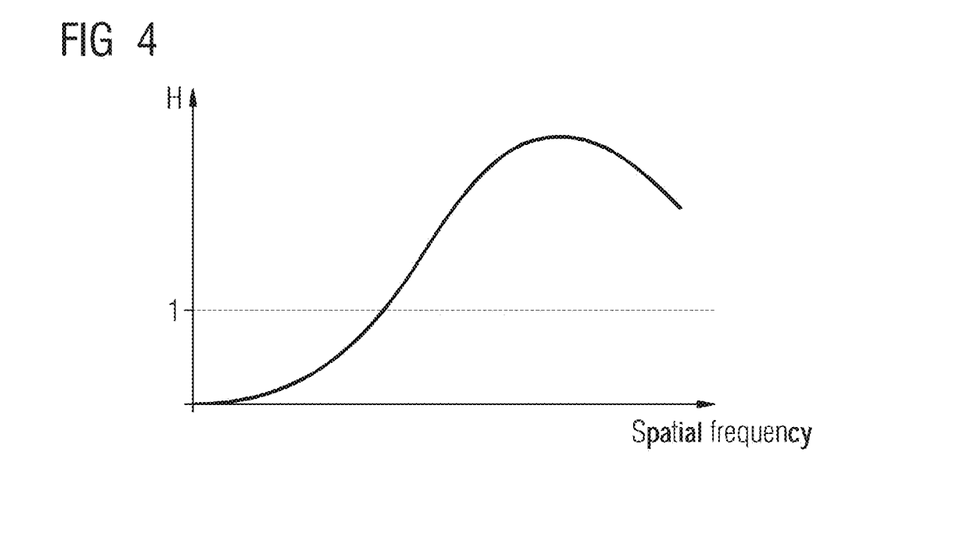
FIG. 4 is an example frequency response of a high-pass filter that is used in an example embodiment of the invention.

Via a high-pass filter H, as shown, for example, in FIG. 4, the image data set I(x,y,z) is transferred in a further step S5 into a contour data set $\Delta(x,y,z)$ according to the formula $$\Delta(x,y,z) = H*I(x,y,z)$$

The high-pass filtration effects an enhancement of higher frequency signals, as is shown by the slope of the curve in FIG. 4 above the value 1. For low-frequency signals, the transfer of the filter moves toward 0 which means that low-frequency image components in the contour data set are not imaged or are only imaged suppressed. Other high-pass filters with quantitatively similar properties can equally be used. In step S6, a multiplication of the contour data set by the local contour significance is carried out. This product conforms to the resultant image data set I'(x,y,z) in accordance with $$I'(x,y,z) = \Delta(x,y,z)*S(x,y,z)$$

Step S6 corresponds to a significance weighting of the contour data. This step causes only the high frequency signal portions in the image data which are significant and consequently are identified as a contour, to be amplified, but not insignificant high frequency signal portions which are formed, for example, by noise. The present method therefore differs from a simpler linear edge enhancement which amplifies without regard to the origin of all the high frequency portions, that is, also the noise.

According to an alternative variant, the above-described product of the contour data set and the local contour significance is added in the form of a correction term to the neutral image data set I'(x,y,z). The resultant image is then given according to $$I'(x,y,z) = I(x,y,z) + \Delta(x,y,z)*S(x,y,z).$$

According to a further variant, the above-described product of the contour data set and the local contour significance is used in the framework of an iterative reconstruction algorithm as an addition to the update term. The resultant image is then given according to $$I_{j+1} = I_j + \alpha[\Lambda(I_j - I_0) + \beta R(I_j) + \gamma S\Delta],$$

where $I_{j+1}$ and $I_j$ denote the image data sets of the j+1-th and j-th iteration. $\alpha$ describes a constant factor which gives the strength of the correction by the update term $[\Lambda(I_j - I_0) + \beta R(I_j) + \gamma S\Delta]$. This is made up essentially as follows: $\Lambda$ is a suitable factor which takes account of the statistics of the image data. R represents a regularization which is applied to the image $I_j$ of the j-th iteration in order to suppress the iteration-related increase of the noise. $\beta$ represents a constant factor which stipulates the mixing strength of the regularization. $\gamma$ represents a constant factor which stipulates the mixing strength of the addition according to the invention.

The resultant image can be subjected subsequently to a segmentation wherein a simple, linear edge detector can be used.

The sequence of steps of the method according to an embodiment of the invention, if not specified by at least one embodiment of the invention itself, is arbitrary and can also be changed without departing from the framework of at least one embodiment of the invention. Individual steps or individual aspects of the example embodiments of the invention are self-evident where useful and are exchangeable with one another within the context of at least one embodiment of the invention.

Figure 5:
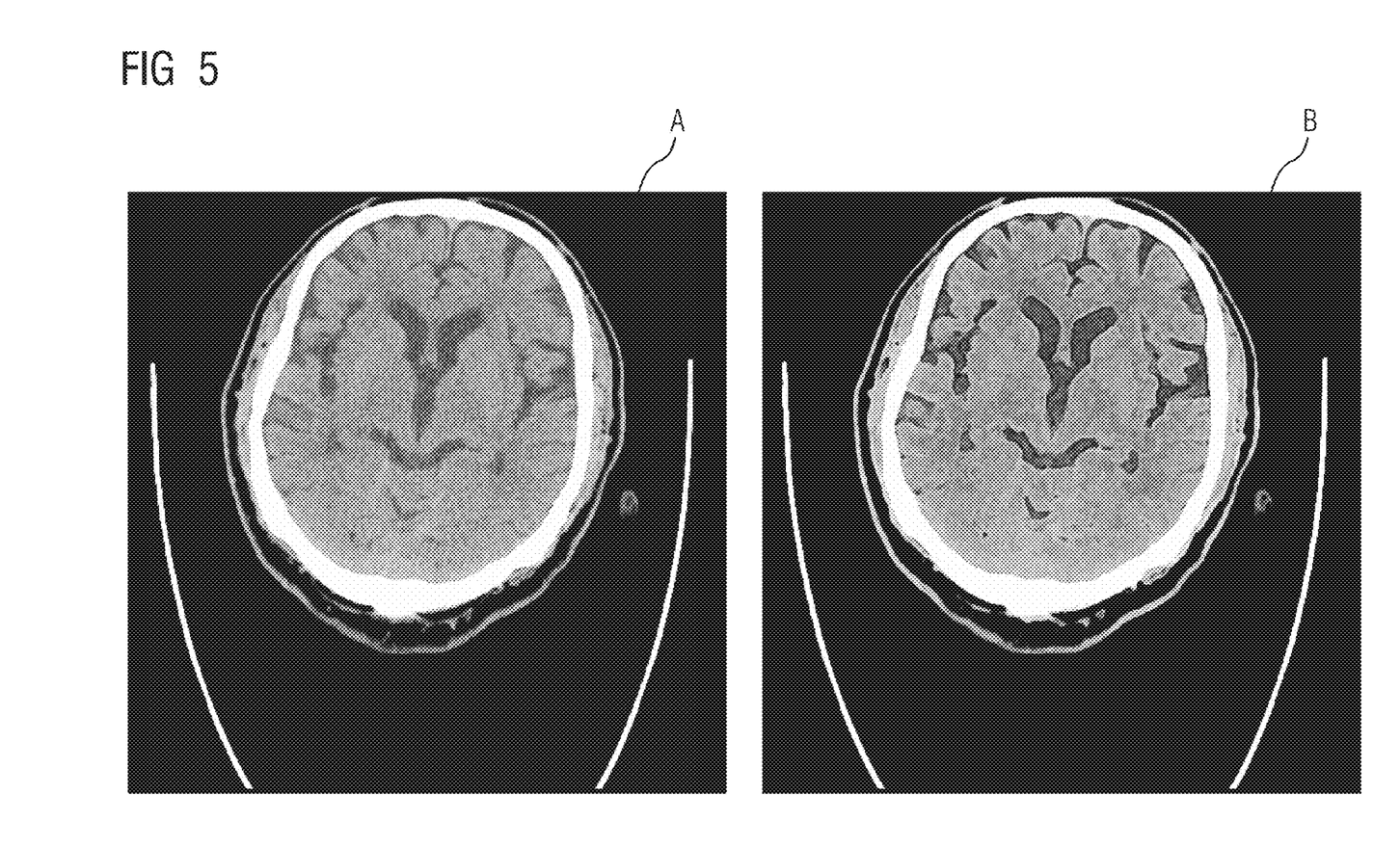
FIG. 5 is an example comparison of reconstructed image data according to the prior art and according to the invention.

By way of example, in FIG. 5, two reconstructed image data sets A, B are compared. For the sake of simplicity, the imaging is carried out 2-dimensionally. Image A corresponds, for example, to an input image data set I(x,y,z), which has been reconstructed in a conventional manner. Image B corresponds to a resultant image data according to an embodiment of the invention I'(x,y,z). Image B has significantly enhanced contrast at the border areas of different tissue types as compared with Image A. Characteristic herein is the light-dark border which is given by the high-pass filtered contour data $\Delta(x,y,z)$. It is simultaneously discernible that the image quality in Image B is retained in comparison with Image A, since the method according to an embodiment of the invention discriminates during the amplification between the contour signal and the noise signal.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for calculating resultant image data of an examination object from scan data acquired during a relative rotation movement between a radiation source of an X-ray image recording system and the examination object, the method comprising:
reconstructing initial image data from the scan data;
deriving contour data from the initial image data;
calculating contour significance data from at least one of the scan data and the initial image data; and
calculating the resultant image data using the contour data and the contour significance data.

2. The method of claim 1, wherein the calculating of the contour significance data comprises calculating local contour information from the initial image data.

3. The method of claim 2, wherein the local contour information comprises at least one of contour amplitude and contour direction.

4. The method of claim 1, wherein the calculating of the contour significance data comprises calculating local, statistical contour information in the initial image data.

5. The method of claim 4, wherein the local statistical information is the local standard deviation of the noise.

6. The method of claim 1, wherein the calculating of the contour significance data comprises determining a contour-to-noise ratio.

7. The method of claim 6, wherein the calculating of the contour significance data comprises forming the contour-to-noise ratio via a restricted significance function to a value between 0 and 1.

8. The method of claim 7, wherein the significance function is configured as a continuous function or as a step function.

9. The method of claim 7, wherein the significance function $f(t)$ takes the following form: $f(t)=1-\exp(-(t/c)^2)$.

10. The method of claim 1, wherein the deriving of the contour data comprises a high-pass filtering of the initial image data.

11. The method of claim 10, wherein the high-pass filtering includes a frequency response the transmission of which disappears at the spatial frequency 0 and increases with increasing spatial frequency greater than 1.

12. The method of claim 1, wherein the resultant image data is calculated on the basis of a product of the contour data and the contour significance data.

13. The method of claim 1, wherein the resultant image data is calculated on the basis of a sum of the initial image data and a product of the contour data and the contour significance data.

14. The method of claim 1, wherein the method is carried out iteratively.

15. A non-transitory computer readable medium including program code for carrying out the method of claim 1 when the program code is run in a computer.

16. A non-transitory machine-readable data carrier including program code for carrying out the method of claim 1 when the program code is run in a computer.

17. A control and computation unit for calculating resultant image data of an examination object from scan data acquired during a relative rotation movement between a radiation source of an X-ray image recording system and the examination object, the control and computation unit comprising:
a memory storing program computer-readable instructions; and
one or more processors configured to execute the instructions such that the one or more processors are configured to,
reconstruct initial image data from the scan data;
derive contour data from the initial image data;
calculate contour significance data from at least one of the scan data and the initial image data; and
calculate the resultant image data using the contour data and the contour significance data.

18. A control and computation unit for calculating resultant image data of an examination object from scan data acquired during a relative rotation movement between a radiation source of an X-ray image recording system and the examination object, the control and computation unit comprising:
a reconstruction unit, configured to reconstruct initial image data from the scan data;
a derivation unit, configured to derive contour data from the initial image data;
a first computation unit, configured to calculate contour significance data from at least one of the scan data and the initial image data; and
a second computation unit, configured to calculate the resultant image data using the contour data and the contour significance data.

19. An X-ray image recording system comprising the control and computation unit of claim 17.

20. The method of claim 2, wherein the calculating of the contour significance data comprises calculating local, statistical contour information in the initial image data.

21. The method of claim 20, wherein the local statistical information is the local standard deviation of the noise.

22. The method of claim 8, wherein the significance function $f(t)$ takes the following form: $f(t)=1-\exp(-(t/c)^2)$.

23. The method of claim 2, wherein the calculating of the contour significance data comprises determining a contour-to-noise ratio.

24. The method of claim 23, wherein the calculating of the contour significance data comprises forming the contour-to-noise ratio via a restricted significance function to a value between 0 and 1.

25. The method of claim 24, wherein the significance function is configured as a continuous function or as a step function.

26. The method of claim 24, wherein the significance function $f(t)$ takes the following form: $f(t)=1-\exp(-(t/c)^2)$.

27. The method of claim 2, wherein the method is carried out iteratively.

28. A non-transitory computer readable medium including program code for carrying out the method of claim 2 when the program code is run in a computer.

29. A non-transitory machine-readable data carrier including program code for carrying out the method of claim 2 when the program code is run in a computer.

30. An X-ray image recording system comprising the control and computation unit of claim 18.

* * * * *